US006306166B1

(12) United States Patent
Barry et al.

(10) Patent No.: US 6,306,166 B1
(45) Date of Patent: Oct. 23, 2001

(54) LOADING AND RELEASE OF WATER-INSOLUBLE DRUGS

(75) Inventors: James J. Barry, Marlboro; Maria Palasis, Wellesley, both of MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/172,026

(22) Filed: Oct. 14, 1998

Related U.S. Application Data

(63) Continuation-in-part of application No. 09/133,603, filed on Aug. 13, 1998, now abandoned, which is a continuation-in-part of application No. 08/910,136, filed on Aug. 13, 1997, now abandoned.

(51) Int. Cl.$^7$ .................................................... A61F 2/06
(52) U.S. Cl. ........................................ 623/1.46; 623/1.42
(58) Field of Search .................................. 604/20, 53, 96, 604/99, 265–266, 890.1, 892.1; 606/192, 194; 623/1.11, 1.42, 1.43, 1.44, 1.45, 1.46

(56) References Cited

U.S. PATENT DOCUMENTS

| | | | |
|---|---|---|---|
| 4,026,296 | 5/1977 | Stoy et al. | 128/349 B |
| 4,481,323 | 11/1984 | Sterling | 524/269 |
| 4,515,593 | 5/1985 | Norton | 604/265 |
| 4,589,873 | 5/1986 | Schwartz et al. | 604/265 |
| 4,603,152 | 7/1986 | Laurin et al. | 604/265 |
| 4,693,243 | 9/1987 | Buras | 128/207.15 |
| 4,769,013 | 9/1988 | Lorenz et al. | 604/265 |
| 4,784,647 | 11/1988 | Gross | 604/178 |
| 4,950,256 | 8/1990 | Luther et al. | 604/265 |
| 5,026,607 | 6/1991 | Kiezulas | 428/423.7 |
| 5,041,100 | 8/1991 | Rowland et al. | 604/265 |
| 5,087,244 | 2/1992 | Wolinsky et al. | 604/53 |
| 5,091,205 | 2/1992 | Fan | 42/72 |
| 5,102,402 | 4/1992 | Dror et al. | 604/265 |

(List continued on next page.)

FOREIGN PATENT DOCUMENTS

| | | | |
|---|---|---|---|
| 0 372 088 A1 | 6/1990 | (EP) | A61L/29/00 |
| 0 379 156 A2 | 7/1990 | (EP) | C08J/7/04 |
| 0 399 712 A1 | 11/1990 | (EP) | A61M/25/10 |
| 0 470 246 (B1) | 2/1991 | (EP) | . |
| 0 623354 | 11/1994 | (EP) | . |
| 0 734 721 (A2) | 3/1996 | (EP) | . |
| 0 747 069 (A2) | 4/1996 | (EP) | . |
| 2112646 A | 7/1983 | (GB) | A61M/25/00 |
| 2 127 839 (A) | 9/1983 | (GB) | . |
| 0 372 088 (A1) | 2/1989 | (JP) | . |
| WO 89/12478 | 12/1989 | (WO) | A61M/29/02 |
| WO 91/08790 | 6/1991 | (WO) | A61M/25/00 |
| WO95/03036 | 2/1995 | (WO) | . |
| WO 96/25176 | 2/1996 | (WO) | . |
| WO99/008729 | 2/1999 | (WO) | . |

OTHER PUBLICATIONS

Cardiovascular and Interventional Radiology, Supplement 1, Sep. 28–Oct. 2, 1997, 158–161.
The Journal of Clinical Investigation, Inc., Sollott, Steven J., Taxol Inhibits Neointimal Smooth Muscle Cell Accumulation after Angioplasty in the Rat, Apr. 1995, vol. 95, 1869–1876.

(List continued on next page.)

Primary Examiner—Sharon Kennedy
(74) Attorney, Agent, or Firm—Kenyon & Kenyon

(57) ABSTRACT

A medical device, polymer composition, and method for delivering substantially water-insoluble drugs to tissue at desired locations within the body. At least a portion of the exterior surface of the medical device is provided with a polymer coating. Incorporated in the polymer coating is a solution of at least one substantially water-insoluble drug in a volatile organic solvent. The medical device is positioned to a desired target location within the body, whereupon the drug diffuses out of the polymer coating.

43 Claims, 11 Drawing Sheets

U.S. PATENT DOCUMENTS

| | | | |
|---|---|---|---|
| 5,135,516 | 8/1992 | Sahatjian et al. | 604/265 |
| 5,232,444 | 8/1993 | Just et al. | 604/96 |
| 5,304,121 | 4/1994 | Sahatjian | 604/53 |
| 5,380,299 | 1/1995 | Fearnot et al. . | |
| 5,383,928 | 1/1995 | Scott et al. . | |
| 5,419,760 | 5/1995 | Narciso, Jr. . | |
| 5,443,496 | 8/1995 | Schwartz et al. . | |
| 5,449,382 | 9/1995 | Dayton . | |
| 5,464,650 | 11/1995 | Berg et al. . | |
| 5,545,208 | 8/1996 | Wolff et al. . | |
| 5,554,182 | 9/1996 | Dinh et al. . | |
| 5,562,922 | 10/1996 | Lambert . | |
| 5,569,463 | 10/1996 | Helmus et al. . | |
| 5,578,075 | 11/1996 | Dayton . | |
| 5,609,629 | 3/1997 | Fearnot et al. . | |
| 5,624,411 | 4/1997 | Tuch | 604/265 |
| 5,629,008 | 5/1997 | Lee . | |
| 5,651,986 * | 7/1997 | Brem et al. | 424/484 |
| 5,674,192 | 10/1997 | Sahatjian et al. | 604/28 |
| 5,674,241 | 10/1997 | Bley et al. . | |
| 5,679,400 | 10/1997 | Tuch . | |
| 5,697,967 | 12/1997 | Dinh et al. . | |
| 5,716,981 * | 2/1998 | Hunter et al. | 514/449 |
| 5,733,925 | 3/1998 | Kunz et al. . | |
| 5,769,883 | 6/1998 | Busccmi . | |
| 5,854,382 * | 12/1998 | Loomis | 528/354 |
| 5,869,127 * | 2/1999 | Zhong | 427/2.12 |
| 5,977,163 * | 11/1999 | Li et al. | 514/449 |

OTHER PUBLICATIONS

Leon, Martin B., MD,Taxol–Coated Coronary Stents: Potential to Reduce Proliferations,3–4.

Heldman, Alan W., et al., Paclitaxel applied directly to stents inhibits neointimal growth thrombotic complications in a procine coronary artery model of restenosis, 2 pages.

Axel, Dorothea I., et al., Paclitaxel Inhibits Arterial Smooth Muscle Cell Proliferation and Migration In Vitro and In Vivo Using Local Drug Delivery, Jul. 15, 1997,636–651.

* cited by examiner

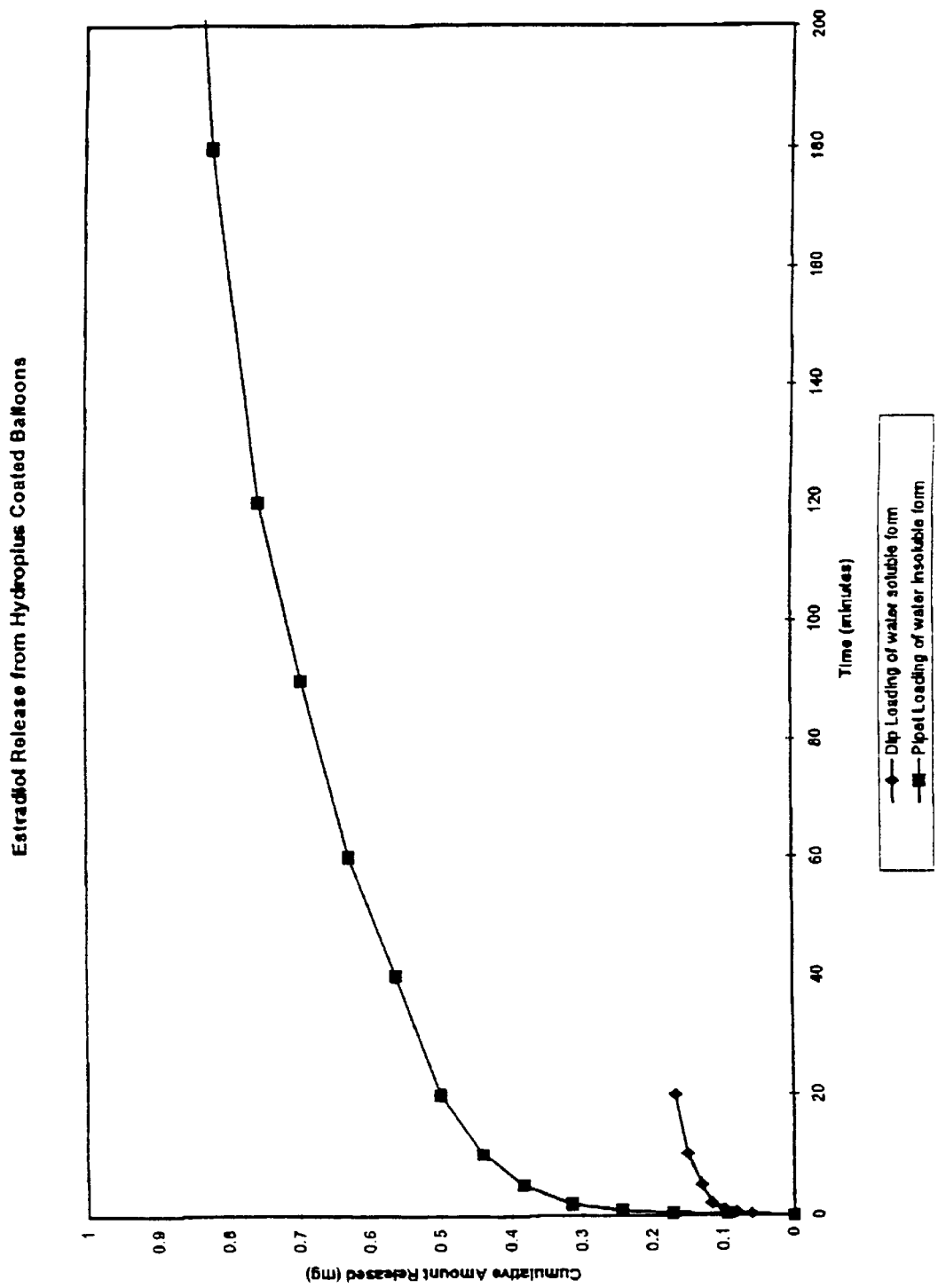

LOADING AND RELEASE OF WATER-INSOLUBLE DRUGS

This application is a continuation-in-part of application Ser. No. 09/133,603, filed Aug. 13, 1998, now abandoned, which is a continuation-in-part of application Ser. No. 08/910,136, filed Aug. 13, 1997, now abandoned, both of which are incorporated herein in their entirety by reference thereto.

FIELD OF THE INVENTION

The invention relates to methods and devices for the localized delivery of substantially water-insoluble drug agents within the body.

BACKGROUND

The systemic administration of drug agents, such as by transoral or intravenous means, treats the body as a whole even though the disease to be treated may be localized. In such a case, systemic administration may not be desirable because, for example, the drug agents may have unwanted effects on parts of the body which are not to be treated, or because treatment of the diseased part of the body requires a high concentration of drug agent that may not be achievable by systemic administration.

It is therefore often desirable to administer drug agents at a localized site within the body. Common examples include cases of localized disease or occluded body lumens. Various methods have been proposed for such localized drug administration. For example, U.S. Pat. No. 5,304,121, hereby incorporated by reference, discloses a method of delivering water-soluble drugs to tissue at desired locations of a body lumen wall. The method generally includes the steps of impregnating a hydrogel polymer on an expandable catheter with an aqueous drug solution, inserting the catheter into a blood vessel to a desired location, and expanding the catheter against the surrounding tissue allowing the release of the drug to the tissue. This method of localized drug delivery using hydrogel polymer impregnation has a limitation of being applicable to drug agents which are dissolved in water at concentrations sufficient for therapeutic gel loading levels. There thus exists a need for a method and apparatus for the localized delivery of drug agents within the body, where the drug agents are substantially water-insoluble. Moreover, there exists a need for a method and implantable device that provides a sustained release of such substantially water-insoluble drug agents over a time frame effective to inhibit proliferative disease.

SUMMARY OF THE INVENTION

One objective of the present invention is to provide a method and apparatus for the localized delivery of substantially water-insoluble drug agents to predetermined locations within the human body.

A further objective of the present invention is to provide a method and apparatus to facilitate gradual, localized release of drug agents at predetermined locations within the human body.

A further objective of the invention is to administer drug agents by diffusion directly into the tissue requiring treatment. The drug is preferably applied in a manner that does not further injure the tissue to be treated, and administration is selectively and evenly distributed over the treated area such that the drug can be taken up by the tissue, without, for example, being washed away by body fluids.

The present invention provides methods and medical devices for the localized delivery of substantially water-insoluble drugs agents.

A particular embodiment of the present invention features a catheter and method for delivering substantially water-insoluble drug agents to tissue at a desired location along body lumen walls. The catheter is constructed for insertion in a body lumen and has a catheter shaft and an expandable portion mounted on the catheter shaft. The expandable portion is expandable to fill the cross-section of the body lumen. At least a portion of the exterior surface of the expandable portion is defined by a polymer coating. Incorporated into the polymer coating is at least one substantially water-insoluble drug. The catheter is positioned to a desired target location within the body, whereupon the polymer coating absorbs water, thus dissolving the drug and resulting in the diffusion of the drug out of the polymer coating. The polymer and drug are selected to allow controlled release of a desired dosage of the drug from the polymer.

Another particular embodiment of the present invention features a stent for the localized delivery of substantially water-insoluble drug agents to tissue at a desired location along body lumen walls. The stent is at least partially coated with a polymer coating having at least one substantially water-insoluble drug therein. The stent configuration, polymer and drug are selected to allow for the controlled release dosage and release rate of the drug from the polymer.

In a most preferred embodiment, the stent is a patterned stent for the localized delivery of paclitaxel to tissue at a desired location along body lumen walls. The stent is at least partially coated with a polymer/paclitaxel matrix that provides sustained release of paclitaxel at the desired site within the lumen wall.

In another aspect of the invention, there is provided a method for preventing or inhibiting proliferative disease in a patient comprising implanting a patterned stent comprising an outer coating of polymer/paclitaxel at a site of cellular proliferation, wherein the paclitaxel is released from the outer coating at a release rate and for a period of time sufficient to inhibit or prevent cellular proliferation at the site.

BRIEF DESCRIPTION OF THE DRAWINGS

FIGS. 7a and 7b show the release profiles of water-soluble and substantially water-insoluble estradiol from balloon catheters having a polyacrylic acid-based coatings for up to 10 and 200 minutes, respectively, in accordance with the present invention.

DETAILED DESCRIPTION

Figure 1A:
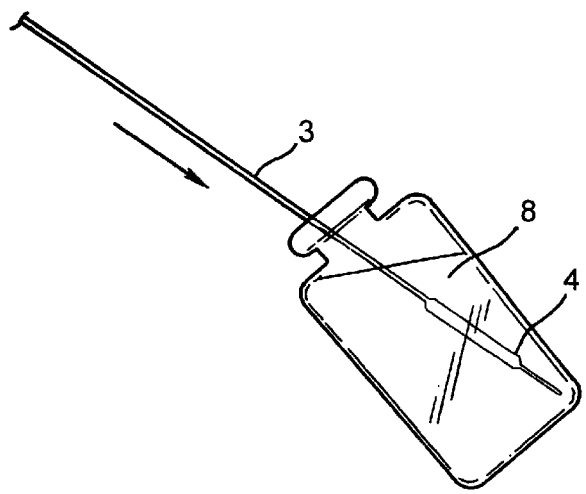
FIG. 1a shows one embodiment of the present invention in which a drug solution is impregnated into a polymer-coated balloon catheter.

The present invention provides methods and medical devices for the localized delivery of one or more substantially water-insoluble drug agents to predetermined locations within the human body, such as within the vascular system, urinary tract, prostate, esophagus, colon, brain, etc.

In accordance with an embodiment of the invention, a substantially water-insoluble drug agent is dissolved in a volatile organic solvent. "Organic solvent" is intended to mean a singular organic solvent or a solvent mixture having at least one organic component. The solvent mixture also includes mixtures of water with miscible organic solvents. The drug solution is then applied to a polymer coating on a medical device that is adapted for insertion into the body. Examples of such medical devices include catheters, guide wires, balloons, filters (e.g., vena cava filters), stents, stent grafts, vascular grafts, intraluminal paving systems, implants and other devices used in connection with drug-loaded polymer coatings. Such devices are implanted or otherwise utilized in body lumina and organs such as the coronary vasculature, esophagus, trachea, colon, biliary tract, urinary tract, prostate, brain, and the like. Examples of suitable vascular grafts are described in U.S. Pat. Nos. 5,509,931, 5,527,353, and 5,556,426. Vena cava filters such as those described in WO 96/12448 and WO 96/17634 may also be used in the present invention. All of foregoing documents identified by number are incorporated herein in their entireties.

The filters that can be provided with a polymeric material/drug-agent matrix in accordance with the present invention include, for example, thrombus filters that can be placed at a selected location within the vascular system and removed when no longer required. A preferred location for placement of these filters is the vena cava. Filters placed in the vascular system can intercept blood clots that may otherwise travel to the lungs and result in a pulmonary embolism, a life-threatening emergency that has become increasingly common. In one embodiment of the present invention there is provided such an implanted vascular filter having a polymeric material/drug outer coating thereon. In a most preferred embodiment, the filter has a polymeric material/paclitaxel outer coating, and most preferably, a polylactic acid/polycaprolactone copolymer/paclitaxel coating. The polymeric coating may also have incorporated therein or thereon any other therapeutic agent that is used for reducing the formation of, or complications due to, clot formation or neointima formation. Such agents, include, but are not limited to antithrombogenic agents and thrombolytic agents and other antiproliferative agents.

Further examples of filters that may be provided with the polymeric material/drug coating in accordance with present invention include, e.g., those described in International Application No. WO 96/17634 and International Application No. WO 96/12448, both of which are herein incorporated by reference.

The grafts, including stent grafts, that can be provided with a polymeric material/drug agent matrix in accordance with the present invention include synthetic vascular grafts that can be used for replacement of blood vessels in part or in whole. A typical vascular graft is a synthetic tube with each end thereof sutured to the remaining ends of a blood vessel from which a diseased or otherwise damaged portion has been removed. In a typical stent graft, each end of the synthetic tube portion includes a stent that is affixed to each of the remaining ends of a blood vessel from which a diseased or otherwise damaged portion has been removed. Alternatively, in a stent graft, the replacement vessel may be segment of a vessel removed from another location in the patient, such as a portion of a femoral artery or the like. In the case of a synthetic graft, the graft is typically tubular and may be, e.g., of a woven, knit or velour construction. Preferred materials for the grafts and covering material for the stent grafts include polyethylene terephthalate and polytetrafluoroethylene. The vascular grafts may be reinforced with, for example, helices, rings, etc. in order to provide uniform strength over the entire surface of the graft tubing. The materials of which such grafts are constructed are biologically compatible materials including, but not limited to, thermoplastic materials such as polyester, polytetrafluoroethylene (PTFE), silicone and polyurethanes. The preferred materials include polyester fibers and PTFE.

Examples of other suitable grafts are described in U.S. Pat. Nos. 5,509,931, 5,527,353, and 5,556,426, all of which are herein incorporated by reference. In a most preferred embodiment of the invention, the graft is provided with a coating of polymeric material/paclitaxel, and most preferably, the polymeric material is a copolymer of polycaprolactone and polylactic acid. This paclitaxel-coated graft, when positioned at a desired site in the body provides an extended release of paclitaxel to the site.

A polymeric material/drug agent matrix in accordance with the present invention may be used as an intraluminal paving system. In such intraluminal paving systems as are known in the art, the polymeric material/drug agent matrix will typically be applied directly to an interior surface of vascular or non-vascular lumina. An intraluminal paving system is formed, for example, by admixing a drug agent with a liquid polymer, in the absence of a solvent, to form a liquid polymer/drug agent mixture. The mixture is then applied directly to a luminal surface by any conventional method, such as by injecting the mixture against the luminal surface. Curing of the mixture typically occurs in-situ. To facilitate curing, a cross-linking or curing agent may be added to the mixture prior to application thereof to the luminal surface. Addition of the cross-linking or curing agent to the polymer/drug agent liquid mixture must not occur too far in advance of the application of the mixture to the luminal surface in order to avoid over-curing of the mixture prior to application thereof to the luminal surface. Curing may also occur in-situ by exposing the polymer/drug agent mixture, after application to the luminal surface, to radiation such as ultraviolet radiation or laser light, heat, or by contact with metabolic fluids such as water at the site where the mixture has been applied to the luminal surface. In a preferred intraluminal paving system in accordance with the invention, the drug agent is paclitaxel and the paclitaxel may be incorporated in the polymeric material alone or in combination with another drug agent. In intraluminal paving systems in accordance with a preferred embodiment of the present invention, the polymeric material incorporating the paclitaxel and, if desired, any additional therapeutic agent (s), may be either bioabsorbable or biostable. Any of the polymers described herein that may be formulated as a liquid may be used to form the polymer/drug agent mixture for use as an intraluminal paving system.

In a preferred embodiment, the polymer used to coat the medical device is provided in the form of a coating on an expandable portion of a medical device. After applying the drug solution to the polymer and evaporating the volatile solvent from the polymer, the medical device is inserted into a body lumen where it is positioned to a target location. In the case of a balloon catheter, the expandable portion of the catheter is subsequently expanded to bring the drug-impregnated polymer coating into contact with the lumen wall. The drug is released from the polymer as it slowly dissolves into the aqueous bodily fluids and diffuses out of the polymer. This enables administration of the drug to be site-specific, limiting the exposure of the rest of the body to the drug.

The polymer used in the present invention is preferably capable of absorbing a substantial amount of drug solution. When applied as a coating on a medical device in accordance with the present invention, the dry polymer is typically on the order of from about 1 to about 50 microns thick. In the case of a balloon catheter, the thickness is preferably about 1 to 10 microns thick, and more preferably about 2 to 5 microns. Very thin polymer coatings, e.g., of about 0.2–0.3 microns and much thicker coatings, e.g., more than 10 microns, are also possible. It is also within the scope of the present invention to apply multiple layers of polymer coating onto a medical device. Such multiple layers are of the same or different polymer materials.

The polymer of the present invention is hydrophilic or hydrophobic, and is selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collage and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment of the invention, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids. In a most preferred embodiment of the invention, the polymer is a copolymer of polylactic acid and polycaprolactone.

By "substantially water-insoluble drug" is meant any therapeutic agent having a greater solubility in organics than in water. More specifically, such drugs have a water solubility of no greater than 1 part drug to 30 parts water, more typically no greater than 1 part drug to 1,000 parts water. Such solubilities are described as "sparingly soluble" to "very slightly soluble" in the art.

The drug agents used in the present invention are selected from a number of drug types depending on the desired application. For example, these drugs include anti-inflammatory agents such as dexamethasone, prednisolone, corticosterone, budesonide, estrogen, sulfasalazine, mesalamine, and analogues thereof; antineoplastic/antiproliferative/anti-miotic agents such as paclitaxel, 5-fluorouracil, cisplatin, vinblastine, vincristine, epothilones, endostatin, angiostatin, thymidine kinase inhibitors, and analogues thereof; anesthetic agents such as lidocaine, bupivacaine, ropivacaine, and analogues thereof; anti-coagulants; and growth factors.

The drug agents useful in accordance with the present invention may be used singly or in combination. For example, an anti-proliferative agent such as paclitaxel may be used in combination with another drug agent, such as an anticoagulant, anti-inflammatory, antithrombogenic, thrombolytic, nitric oxide-containing polymer, or a vascular cell promoter such as VEGF, for example.

Paclitaxel is a preferred drug agent for use in accordance with the present invention either alone or in combination with another drug agent, as described above. Paclitaxel is a complex alkaloid extracted from the Pacific Yew Taxusbrevifolia Family (Family Taxacea) which has been demonstrated to have antiproliferative activity. As used herein, paclitaxel includes the alkaloid and any pharmacologically active derivative or analog thereof. Thus paclitaxel includes naturally occurring forms and derivatives thereof and synthetic and semi-synthetic forms thereof. TAXOL® is a commercially available form of paclitaxel.

In accordance with the present invention, the drug agents are dissolved in a volatile organic solvent such as, for example, ethanol, isopropanol, chloroform, acetone, pentane, hexane, or methylene chloride, to produce a drug solution. In the case of paclitaxel the preferred solvent is chloroform. The drug solution is then applied to the polymer. A volatile organic solvent typically is selected to provide drug solubilities much greater than the corresponding aqueous solubility for the substantially water-insoluble drug. Accordingly, application of the drug solution to the polymer often results in drug loadings that are orders of magnitude greater than loadings that can be achieved by application of a saturated aqueous solution of the drug to the polymer.

The drug solution is applied to the polymer coating by any suitable means, including dipping the polymer coating into the drug solution or by applying the solution onto the coating such as by pipet or by spraying, for example. In the former method, the amount of drug loading is controlled by regulating the time the polymer is immersed in the drug solution, the extent of polymer cross-linking, the concentration of the drug in the solution and/or the amount of polymer coating. In another embodiment of the invention, the drug is incorporated directly into the polymer prior to the application of the polymer topcoat as a coating onto a medical device.

After applying the drug solution to the polymer coating, the volatile solvent is evaporated from the coating, for example, by drying in air or in an oven.

The release profile of the drug from the polymer coating is determined by many factors including the drug solubility, amount of drug applied and the thickness and porosity of the polymer coating.

In a preferred embodiment of the present invention, one or more additional layers may be applied over at least a portion of a medical device previously coated with a polymer/drug agent in accordance with the present invention. Desirably, such an additional layer will be provided to modify or modulate the release of one or more of the drug agents in the underlying layer. For example, a polymeric coating may be applied over the previously applied polymer/drug agent coating to modulate the release rate of the drug agent in that layer. This additional release rate-modifying or modulating layer may be applied in a subsequent coating step in a manner similar to that disclosed herein, for example by spraying a polymer solution onto the previously applied coating layer or by dipping the previously coated medical device into a solution of the polymer selected to form the modifying or modulating layer. However, other methods for applying polymeric materials to substrates, including, for example, in-situ polymerization methods such as plasma polymerization may also be used to provide the additional release rate-modifying or modulating polymeric layer. Such other application processes included within the scope of the present invention are those that will not detrimentally affect the previously applied layer, including the drug agent(s) incorporated therein or thereon. The additional layer may also include one or more additional drug agents including any of the drug agents incorporated into the underlying polymer/drug agent coating layer. Prior to application of the modifying or modulating layer, any conventional adhesion promotion agent may be applied to the previously applied coating, or other treatment thereof may be conducted, in order to promote adhesion of the modifying or modulating layer to the previously applied coating. Where the modifying or modulating layer is applied in a manner similar to the underlying layer, the polymeric material used for the modifying or modulating layer can be any of the polymers described herein. Where such polymeric material is applied, for example, by plasma polymerization, the polymers are those that can be formed by monomers in a gas phase that can be activated for example by radio frequency waves. Such monomers include, for example, silicone-based monomers such as cyclic or acyclic siloxanes, silanes, silylimidazoles; fluorine-based monomers such as hydrofluorocarbons; aliphatic or aromatic hydrocarbons; acrylic monomers; and combinations thereof. The monomer gas may have functional groups that facilitate later attachment of drug agents thereto by covalent bonding, for example. Any appropriate polymer for the modifying or modulating layer is preferably selected to have a porosity that provides the modifying or modulating effect as described above. The porosity of this polymeric material may also be modified by addition of porosigens or other porosity-effecting adjuvants that are conventionally added to polymers for this purpose. Other factors guiding the selection of a modulating or modifying polymer include, but are not limited to, the thickness of coating layer, the tortuosity of the polymeric material affecting the path of resistance to drug mobility within the polymeric material, the cross-linking density, drug solubility in the modulating or modifying layer, etc. The thickness of the modifying or modulating layer will preferably be less than 5,000 Å, and more preferably in the range of from about 50–2000 Å. A preferred modifying or modulating polymer in accordance with the present invention is a siloxane polymer formed, for example, by a plasma polymerization process. This siloxane modifying or modulating polymer is preferably applied to a medical device that has a polyurethane/drug agent coating previously applied thereto in accordance with the present invention.

When an expandable member such as a balloon catheter is used to administer the drug, pressure can be used to increase the rate of drug transfer to the tissue. An increase in pressure increases the diameter of the balloon and therefore the diameter of the surrounding tissue, thereby increasing the surface area for drug transfer. The amount of drug that is delivered per unit time is therefore increased.

When an expandable catheter is chosen as the medical device of the present invention, the expandable portion is preferably a balloon, in which case the drug is placed in the polymer for controlled release of the drug upon expansion of the balloon against a body lumen. The expandable portion optionally includes a stent, mountable in a body lumen by expansion thereof. The catheter also optionally comprises a sheath member which is extendable over the expandable portion to inhibit release of the drug into body fluids during placement of the catheter.

Figure 1B:
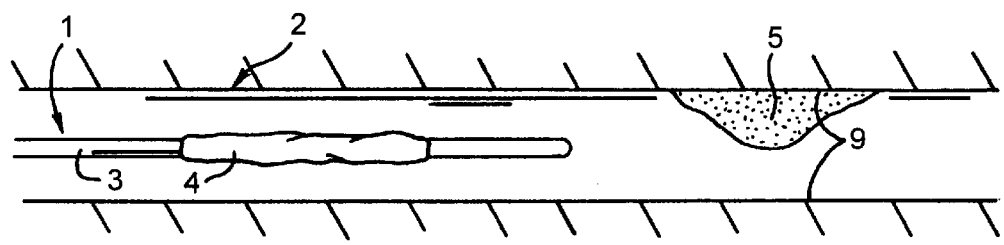
FIG. 1b shows the insertion of a polymer-coated balloon catheter into a body lumen, in accordance with the present invention.
Figure 1C:
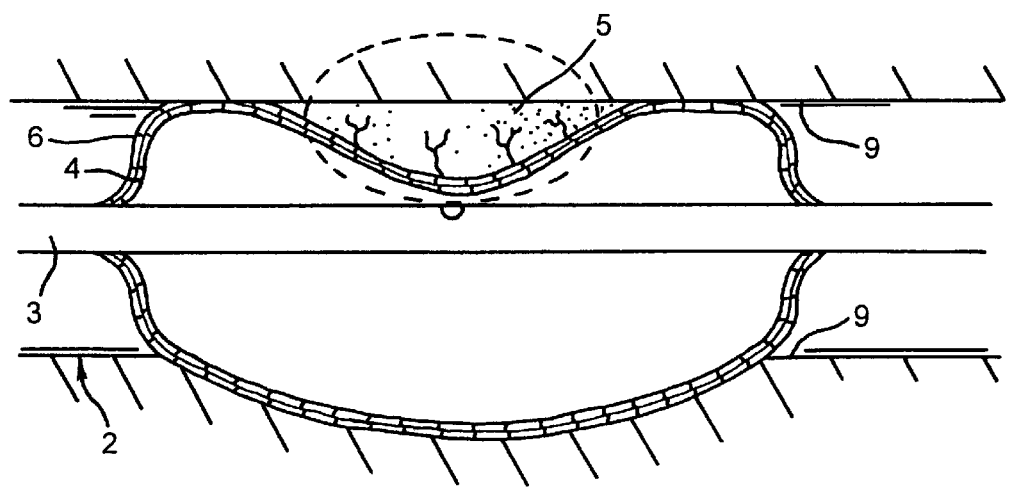
FIG. 1c shows the expansion of a polymer-coated balloon catheter at an occlusion site within a body lumen, in accordance with the present invention.

Referring now to FIGS. 1a–1c, an embodiment for the localized delivery of substantially water-insoluble drugs to a predetermined location within the body is described. The drug administration method shown in FIGS. 1a–1c illustrates the use of the present invention in conjunction with an angioplasty process. Catheter device 1 comprises a body 3 having a balloon 4 attached at its distal end. The balloon 4 on the catheter 3 includes a polymer coating 6. As shown in FIG. 1a, drug solution 8 is impregnated into the polymer coating with the balloon in its substantially deflated state prior to insertion into the patient. As shown in FIG. 1b, after the volatile solvent is evaporated, the device 1 is inserted into a body lumen 2 having a region to be treated, such as an occlusion due to a deposition of plaque 5 on the lumen wall tissue 9. The device 1 is moved along the vessel to position the balloon 4 at the occlusion site, as shown in FIG. 1c. The lumen may be, for example, a narrow, tortuous opening through which the catheter is passed by torquing or other known techniques. As shown in FIG. 1c, the balloon is inflated to provide close contact between the drug-impregnated polymer coating 6 and the surrounding plaque and tissue. As water from the body penetrates into the polymer coating 6, it begins to dissolve the drug agent, which subsequently diffuses out of the polymer coating 6 and into the surrounding plaque and tissue.

During drug administration, a substantial amount of the drug contained in the polymer coating is diffused into the affected area. The inflation pressure needed to expand the balloon catheter and dilate the lumen, if necessary, is typically in the range of about 1 to 20 atm. The balloon is formed of any suitable materials such as vinyl polymers such as polyethylene; polyesters such as polyethylene terephthalate; polyamides such as nylon; polyolefins and copolymers thereof (e.g., Selar, Pebax, Surlyn, Hytrel, etc.). The balloon is optionally a perfusion balloon, which allows blood to perfuse the catheter to prevent ischemia during delivery. A perfusion balloon is particularly preferred for long arterial delivery times and when the delivery drug is only very slightly soluble in water.

Figure 2:
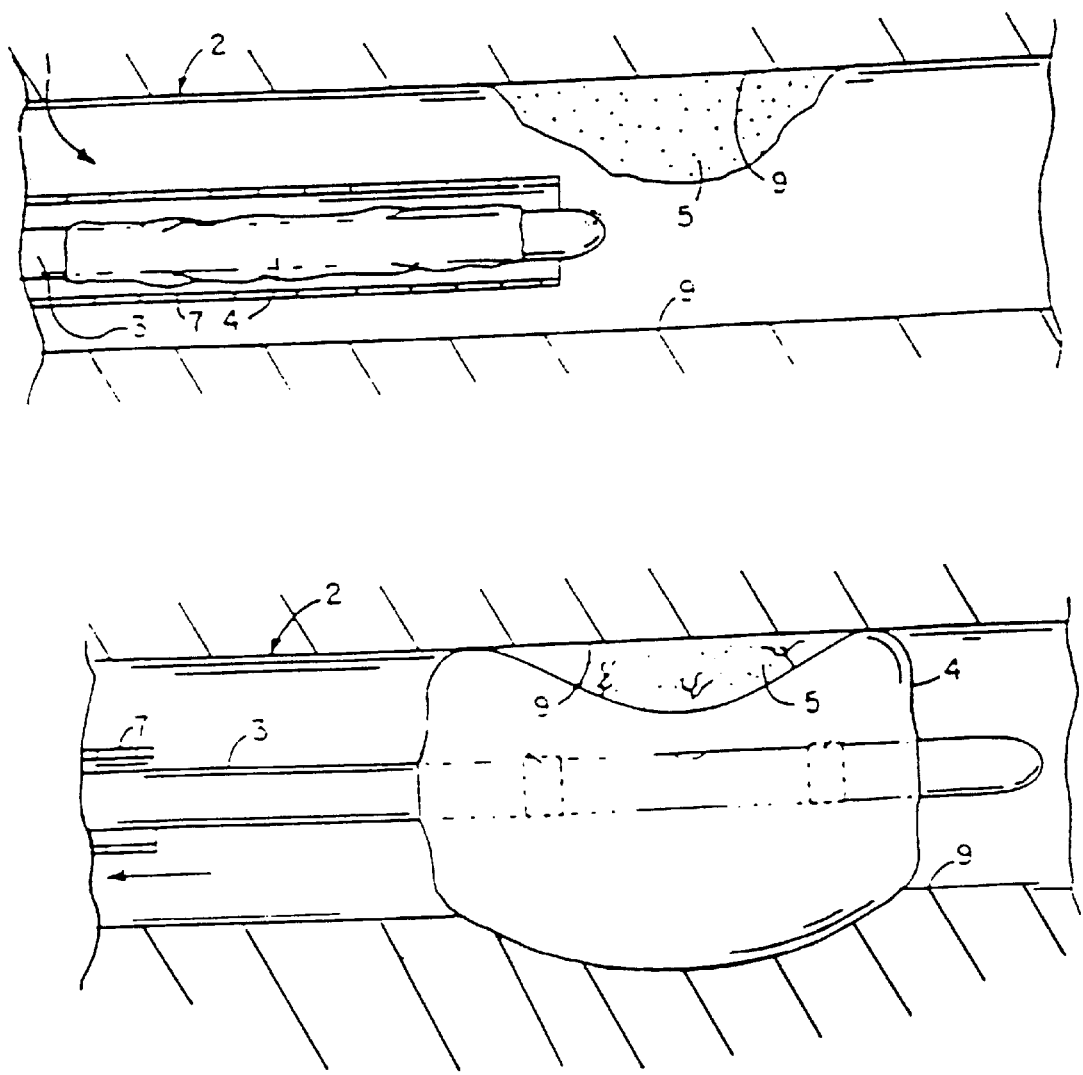
FIG. 2 shows a drug delivery balloon catheter embodiment of the present invention including a sheath for covering the catheter as it is being moved through a vessel toward the occlusion to be treated.

Referring to the embodiment of the invention illustrated in FIG. 2, the balloon portion 4 of catheter 3 is optionally covered by a protective sheath 7 while the instrument 1 is inserted into a body lumen 2 and positioned at a treatment region. As the coated balloon 4 is positioned at occluded site 5, the protective sheath 7 is drawn back to expose the balloon 4. In an alternative embodiment, the sheath remains stationary while the catheter moves the coated balloon forward into the occluded region. The sheath 7 protects the coating and inhibits premature release of the drug. Such a sheath might be particularly advantageous when using drugs which are not sufficiently water-insoluble or if even minor delivery to tissue during catheter placement is a problem, e.g. for extremely toxic drugs.

Although FIGS. 1 and 2 illustrate the application of the present invention to an angioplasty process, the present invention is also used to administer drug agents to target locations where there is no occlusive formation.

In other embodiments, the medical device of the present invention is an implantable medical device such as a stent, covered stent, stent graft, intraluminal paving system, wire guide, cannulae, artificial limbs, joints, and other prosthetic devices. Where a stent is used it may either balloon- or self-expandable, and is constructed of any biocompatible material. The grafts and covering materials for the stent grafts are made of any biocompatible material such as, for example, polyurethane, polyesters, silicone, or polytetrafluoroethylene.

Stents are generally configured in one of two configurations: patterned or coil. Coil-type stents include, for example, wire stents in the form of coils, spirals or the like, with or without spines, an example of which is the subject of U.S. Pat. No. 4,886,062 (incorporated herein by reference), another example of which is the GR-II® (Cook Inc.) stent. Patterned stents used in accordance with a most preferred embodiment of the invention include all stents other than coil-type stents such as, for example, slotted tube stents, criss-cross tubular stents, braided stents, hexagonal stents, nets, articulated stents, and the like. Patterned stents are also generally preferred over coil stents because they provide more radial support for surrounding body lumina. Preferred patterned stents for use in the present invention include the NIR™ and RADIUS™ stents (SCIMED Life Systems, Inc.) as described in U.S. Pat. No. 5,733,303 and WO 96/26689 (both of which are incorporated herein by reference); the WALLSTENT® (Schneider Inc.) as described in U.S. Pat. Nos. 4,655,771 and 5,061,275 (both of which are incorporated herein by reference); and the SYMPHONY® stent (Boston Scientific Corp.) as described in U.S. Pat. No. 5,540,712 (incorporated herein by reference). The stents and stent grafts described in U.S. Pat. Nos. 5,766,237, 5,681,356, 5,522,881 and 5,776,180 (each of which is incorporated herein by reference) and the polymer stents described in U.S. Pat. No. 5,769,883 (incorporated herein by reference) are also within the scope of the present invention.

The implantation of a stent, stent graft, vascular graft or filter in accordance with the present invention can be conducted by any medical procedure conventionally used for such implantation. In the case of a stent, a polymer/paclitaxel coated stent in accordance with the present invention can be fitted over the inflatable element of a balloon catheter and expanded by the balloon to force the stent into contact with the body lumen at or near a site of injury such as, for example, within an injured blood vessel.

Where the medical device in accordance with the present invention is, e.g., a catheter, stent, graft, filter, etc., or any other device used in the vascular system, any blood vessel including arteries, veins and capillaries may be treated in accordance with the present invention. These blood vessels may be in or near any organ in the human or mammalian body.

In a most preferred embodiment of the invention, a patterned stent having a polymer/paclitaxel coating is used to prevent or inhibit proliferative disease. As used herein, "proliferative disease" means any disease or disorder including cancers, malignancies, benign growths and other conditions that result from hyperactivity or hyperplasia of somatic cells, and includes restenosis and vascular hyperplasia such as neointimal hyperplasia. Such proliferative diseases may occur in vascular and other luminal or non-luminal regions of the body.

Figure 10:
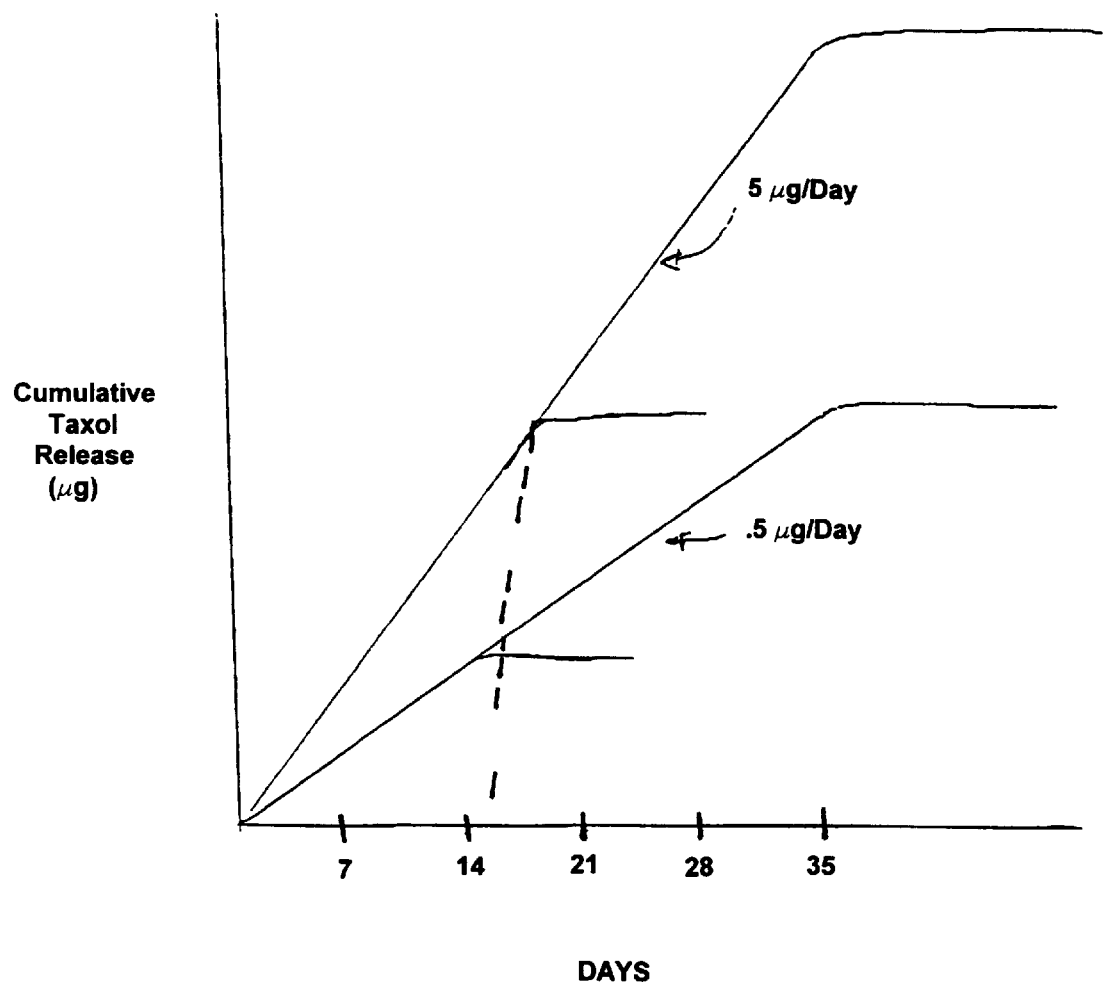
FIG. 10 shows the cumulative release profile of paclitaxel over a time frame of days. This figure shows the cumulative release of paclitaxel for delivery rates of 5 μg/day and 0.5 μg/day.

The inventors have surprisingly found that extended drug release of paclitaxel from a polymer coating on a patterned stent is obtained and consequently, a significant reduction in neointima formation results. The reduction in neointima formation obtained with patterned stents used in accordance with the present invention is surprisingly superior to that obtained using a coiled stent coated with a polymer/paclitaxel matrix. FIG. 10 shows the release rate of paclitaxel obtained with a stent in accordance with the present invention. In a preferred embodiment, paclitaxel is released from a polymer/paclitaxel coated stent for a time period of at least about 28 days after implantation of stent at the desired location within the body. The patterned stent is coated with an outer coating of polymer/paclitaxel such that the amount of paclitaxel is sufficient to prevent, decrease, eliminate or modify cellular proliferation associated with proliferative disease or disorder. The amount of paclitaxel sufficient to inhibit or prevent proliferative disease will vary according to the size of the patterned stents, but is generally in the range of from about 50 $\mu$g to 500 $\mu$g per stent.

Procedures for preparing a drug delivery medical device with a polymer coating are presented in the following non-limiting examples.

EXAMPLE 1

Release Kinetics of Paclitaxel from Polyacrylic Acid-based Coating

Figure 3A:
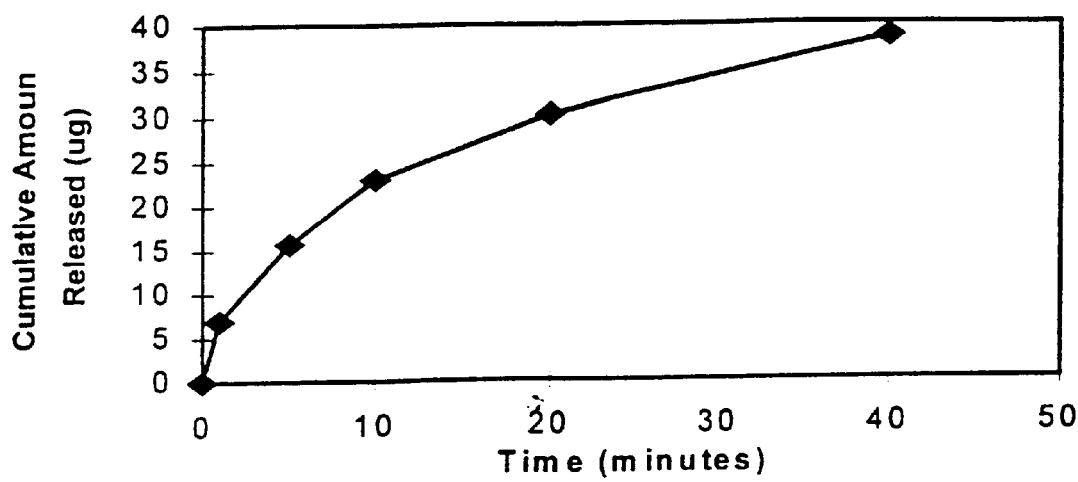
FIGS. 3a and 3b show the release profile of paclitaxel from a balloon catheter having a polyacrylic acid-based coating for up to 50 and 5000 minutes, respectively, in accordance with the present invention.
Figure 3B:
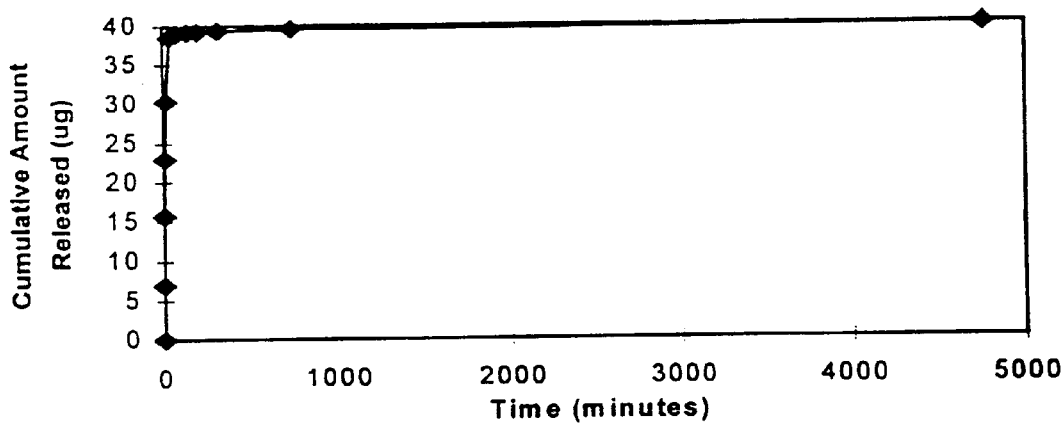

A 2 mg/ml solution of paclitaxel is prepared in chloroform. The solution is gently agitated until the paclitaxel is completely dissolved. The solution is applied via pipet to a balloon catheter having a polyacrylic acid-based coating and inflated to 2 atm. A total of 100 $\mu$l of solution, and hence 200 $\mu$g of paclitaxel, is applied to the catheter. The balloon catheter is then dried in air for 30 minutes and in a vacuum oven for 48 hours at 50° C. to evaporate the chloroform. The catheter is then immersed in a solution of 1% dimethyl sulfoxide (DMSO) and phosphate buffered saline(PBS) having a pH of 7.4 for in-vitro drug release. The cumulative amount of paclitaxel released from the catheter coating yields the data shown in FIGS. 3a and 3b.

EXAMPLE 2

Release Kinetics of Dexamethasone from Polyacrylic Acid-based Coating

Figure 4A:
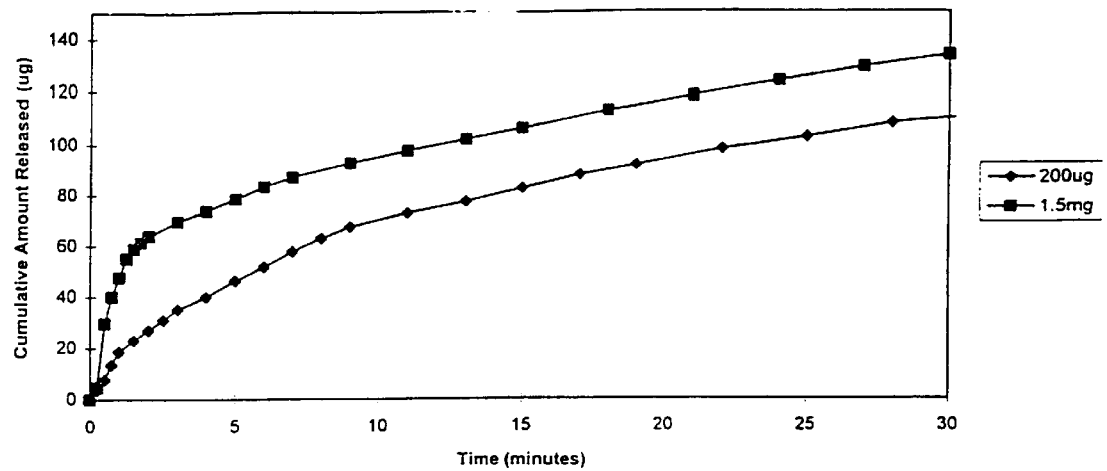
FIGS. 4a and 4b show the release profile of dexamethasone from a balloon catheter having a polyacrylic acid-based coating for up to 30 and 400 minutes, respectively, in accordance with the present invention.
Figure 4B:
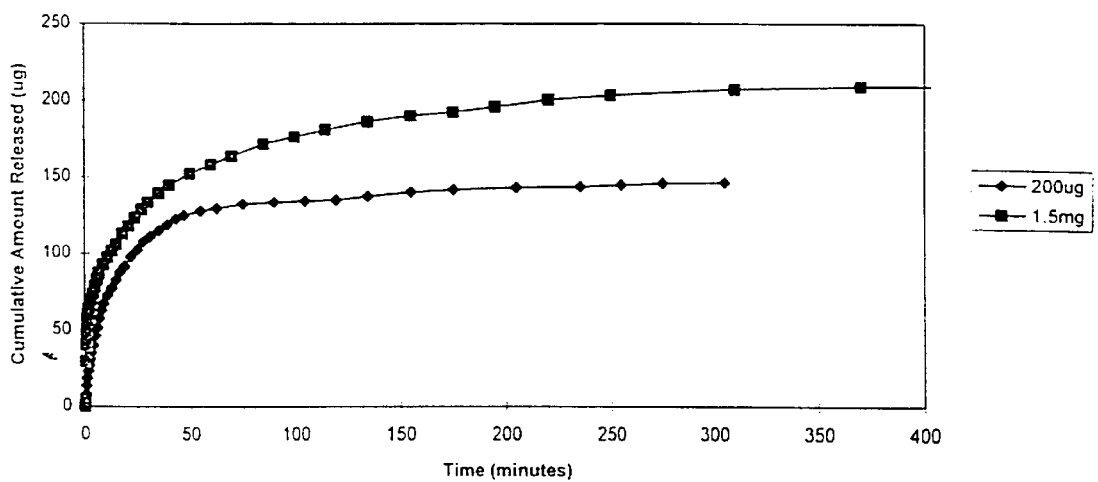

Solutions containing 1.5 mg/ml and 200 $\mu$g/ml of dexamethasone in chloroform, are prepared by gently agitating until the dexamethasone is completely dissolved. The solutions are separately applied via dripping to separate balloon catheters having polyacrylic acid-based coatings and inflated to 2 atm. A total of 100 µl of each solution is applied to each respective catheter, corresponding to dexamethasone loadings of 1.5 mg and 200 µg, respectively. These results can be contrasted with the inability to apply substantial amounts of dexamethasone to polyacrylic acid-based coatings using aqueous solutions, in which case only about 1 µg of dexamethasone can be loaded into such coatings. The balloon catheters are then dried in a vacuum oven for 2 hours at 50° C. to evaporate the chloroform solvent. The catheters are thereafter immersed in PBS (pH=7.4) to track the release of dexamethasone over time. The cumulative amount of dexamethasone released from each catheter yields the data shown in FIGS. 4a and 4b.

EXAMPLE 3

Release Kinetics of Molsidomine from Polyacrylic Acid-based Coating

Figure 5:
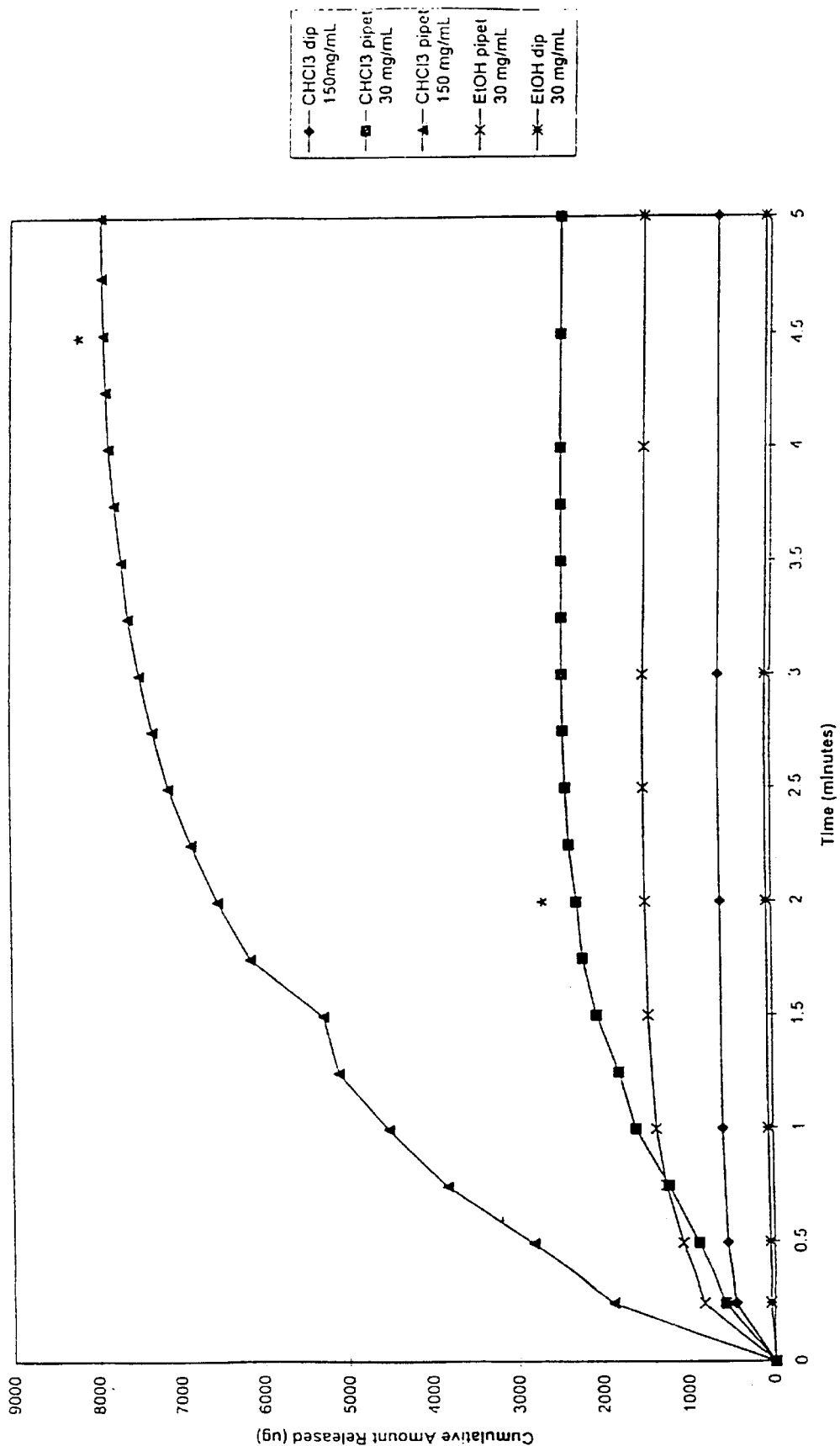
FIG. 5 shows the release profiles of molsidomine from various balloon catheters having a polyacrylic acid-based coating for up to 5 minutes, in accordance with the present invention.

Various solutions of molsidomine in volatile solvents are prepared and applied to balloon catheters by the methods indicated in Table I. In the "dip" application technique, each balloon catheter having a polyacrylic acid-based coating is dipped into its respective solution for 10 minutes. In the "pipet" application technique, 200 µl of solution is pipetted onto its respective coated balloon catheter while slowly turning. All samples are dried in an oven for 30 minutes at 50° C. and thereafter immersed in PBS (pH=7.4) to track the release of molsidomine over time. The cumulative amount of molsidomine released from each catheter yields the data shown in FIGS. 5a and 5b.

TABLE I

Molsidomine solution characterization, and methods of applying molsidomine solution to polymer coated catheters.

| Sample | Solvent | Concentration (mg Molsidomine per ml solvent) | Application technique |
| --- | --- | --- | --- |
| 1 | chloroform | 150 | dip |
| 2 | chloroform | 30 | pipet |
| 3 | chloroform | 150 | pipet |
| 4 | ethanol | 30 | pipet |
| 5 | ethanol | 30 | dip |

EXAMPLE 4

Figure 6:
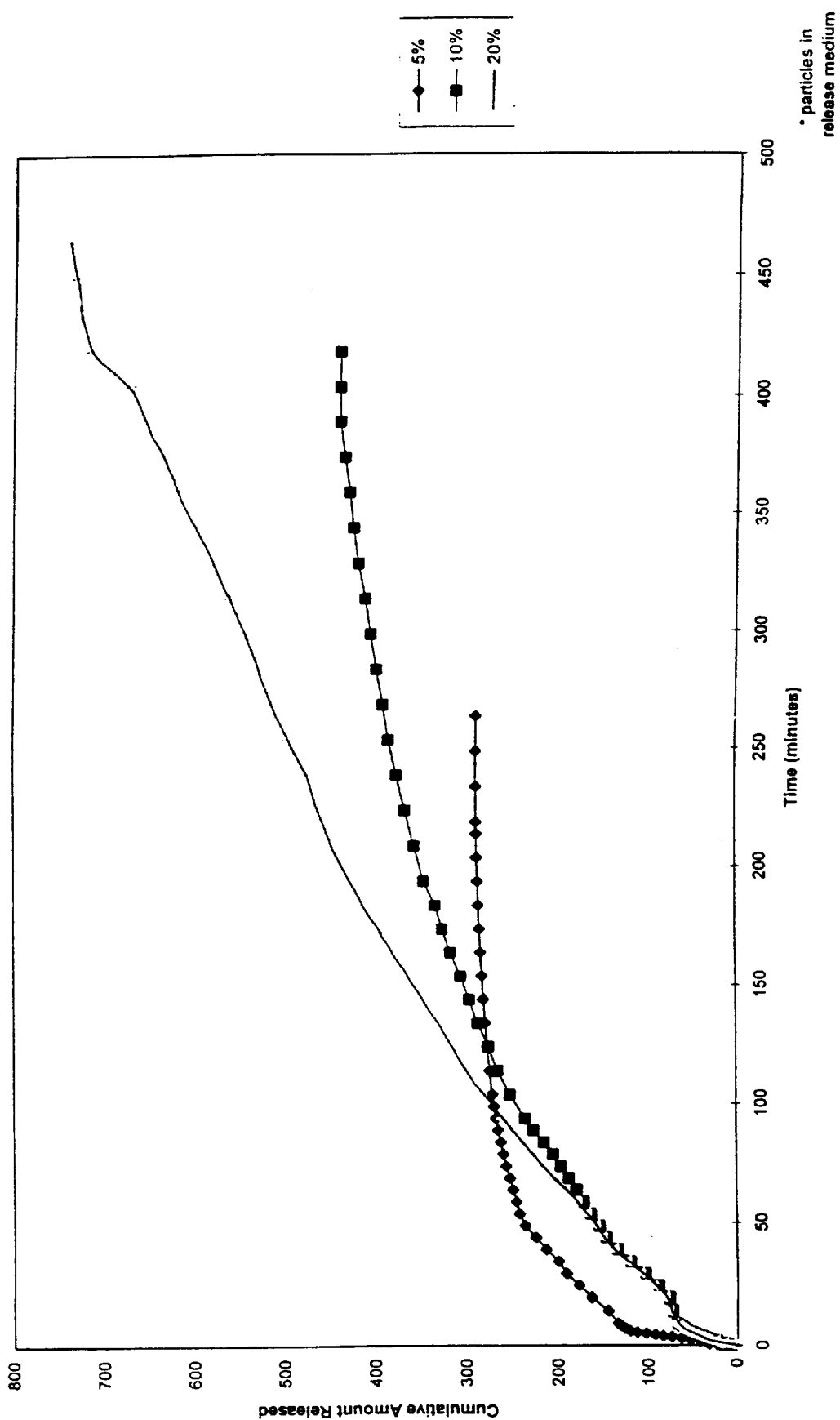
FIG. 6 shows the release profiles of dexamethasone from various balloon catheters having a polyacrylic acid-based coating for up to 450 minutes, in accordance with the present invention.

Release Kinetics of Dexamethasone Added to Polyacrylic Acid-based Topcoat Formulation Rather than forming a solution of dexamethasone in an organic solvent and then applying this solution to polymer-coated balloon catheters as in Example 2, dexamethasone is added directly to the polymer used to coat the balloon catheters. Dexamethasone is weighed out into 0.05 g, 0.1 g, and 0.2 g samples, each of which is each added to 1 ml lots of polymer topcoat solution containing polyacrylic acid, methyl ethyl ketone, dimethyl formamide, and t-butyl alcohol. The dexamethasone samples are mixed with the polymer topcoat solutions until completely dissolved. The dexamethasone-containing polymer topcoat solutions are separately applied via dripping to separate, uncoated balloon catheters inflated to 2 atm. After drying in a vacuum oven for 2 hours at 50° C., the catheters are immersed in PBS (pH=7.4) to track the release of dexamethasone over time. The cumulative amount of dexamethasone released from each catheter yields the data shown in FIG. 6.

EXAMPLE 5

Comparative Release Kinetics for Water-soluble and Water-insoluble Estradiol

Figure 7A:
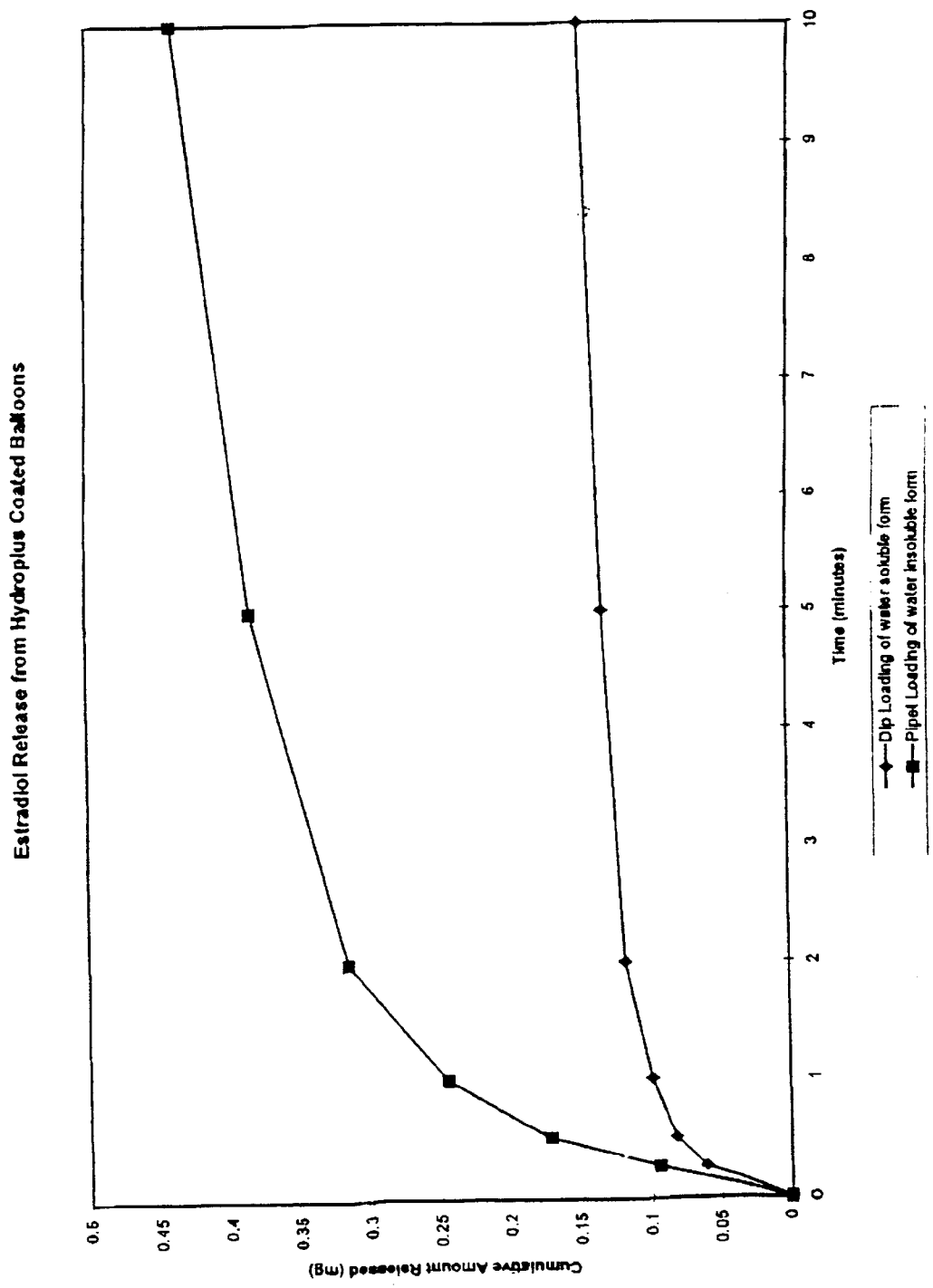

Estradiol is provided in both water-soluble and substantially water-insoluble forms. Water-soluble estradiol is applied to a balloon catheter coated with a polyacrylic acid-based coating by i) preparing a 10 mg/ml solution of water-soluble estradiol in deionized, ultra-filtered water; and ii) placing the balloon catheter, inflated to 2 atm, into 200 µl of the solution for 20 minutes. Water-insoluble estradiol is applied to a balloon catheter coated with a polyacrylic-acid based coating by i) preparing a 10 mg/ml solution of substantially water-insoluble estradiol in methanol; and ii) dripping 100 µl of the solution onto the balloon catheter. The catheters are thereafter immersed in PBS (pH=7.4) to track the release of both water-soluble and water-insoluble estradiol over time. Greater release is observed for the substantially water-insoluble form of estradiol when compared to the water-soluble form. The cumulative amount of estradiol released from each catheter yields the data shown in FIGS. 7a and 7b.

EXAMPLE 6

In-vivo Delivery of Paclitaxel from Polyacrylic Acid-based Coating

A 9.8 mg/ml solution of radio-labeled paclitaxel in chloroform is prepared. A total of 50 µl of the solution is applied via pipet to a balloon catheter having a polyacrylic acid-based coating. The paclitaxel from the coated balloon catheter is then released in-vivo to porcine arteries. After release for a predetermined amount of time, the paclitaxel remaining in the coating is extracted using two sequential ethanol washes. The amount of paclitaxel released in the pig bloodstream, as calculated from the amount of paclitaxel loaded into the coating minus that extracted from the coating after delivery, is shown in Table II.

TABLE II

Amount of paclitaxel released into pig bloodstream from an impregnated, polyacrylic acid-based coated balloon catheter, as a function of delivery time.

| Amount of time in bloodstream | Amount of paclitaxel extracted from balloon after delivery (µg) | Amount of paclitaxel released in bloodstream (µg) | % of paclitaxel released in bloodstream |
| --- | --- | --- | --- |
| 1 minute | 182 + 1 | 307 | 63 |
| 5 minutes | 160 + 30 | 330 | 68 |

EXAMPLE 7

Delivery of Paclitaxel to Explanted Porcine Arteries from Polyacrylic Acid-based Coating A 9.8 mg/ml solution of radio-labeled paclitaxel in chloroform is prepared. A total of 50 µl of the solution is applied via pipet to a balloon catheter having a polyacrylic acid-based coating. The coated balloon catheter is then delivered to an explanted porcine artery for 15 minutes. After delivery, the paclitaxel remaining in the coating is extracted using two sequential ethanol washes. The delivered paclitaxel is extracted from the vessel, also by using two sequential ethanol washes. In addition, the vessel is placed in tissue solvent and counted for paclitaxel. Using these extraction methods, at least 80% of the paclitaxel loaded onto the balloon catheter is recovered, as shown in Table III.

TABLE III

Paclitaxel recovery from ex vivo delivery to porcine artery.

| | |
| --- | --- |
| Amount paclitaxel loaded onto balloon | 489 µg |
| Amount paclitaxel extracted from the balloon after delivery | 360 µg |
| Amount paclitaxel extracted from artery | 30 µg |
| Amount paclitaxel counted from tissue solution | 1 µg |
| Total paclitaxel measured | 391 µg |
| Percentage of paclitaxel recovered | 80% |

EXAMPLE 8

Release Kinetics of Paclitaxel from Polyurethane-based Stent Coating

Slotted tube stainless steel stents are coated with polyurethane by spraying a 1 wt % solution of CHRONOFLEX® polyurethane (made by CT Biomaterials) in tetrahydrofuran directly onto the stent surface. The coated stents are dried in a vacuum oven for three hours at 70° C.

Each polyurethane coated stent is placed in a vial, which is filled to maximum volume (1.5 ml) with a solution of paclitaxel in ethanol, and sealed. The stent is stored in the vial for three days at room temperature. The stent is then removed from the vial and dried for one hour at 65° C.

The above procedure is conducted using solutions of varying concentrations. Each stent is analyzed for paclitaxel content by extraction in dichloromethane solvent. The results are presented in Table IV below. Samples 1 and 2 were obtained using a paclitaxel concentration of 10 mg/ml, samples 3 and 4 using a 20 mg/ml solution and sample 5 and 6 using a 30 mg/ml solution.

TABLE IV

| | Paclitaxel content. | | | |
| --- | --- | --- | --- | --- |
| Sample # | Paclitaxel conc. (mg/ml) | Paclitaxel content (µg) | Coating Wt. (µg) | µg Paclitaxel per µg coating |
| 1 | 10 | 44.8 | 796 | 0.06 |
| 2 | 10 | 88.2 | 859 | 0.10 |
| 3 | 20 | 151.2 | 718 | 0.21 |
| 4 | 20 | 127.6 | 702 | 0.18 |
| 5 | 30 | 157.1 | 736 | 0.21 |
| 6 | 30 | 144.3 | 629 | 0.23 |

These results suggest that paclitaxel loading is relatively independent of paclitaxel concentration above 20 mg/ml, assuming equilibrium is attained in the three-day period. Nevertheless, the 30 mg/ml paclitaxel concentration is chosen for release studies as it produces the maximum paclitaxel loading (21–23%), while still being sufficiently below the saturation concentration for paclitaxel in ethanol (39 mg/ml).

Seven polyurethane coated stents are loaded using a 30 mg/ml paclitaxel solution, removed and dried as set forth above. Paclitaxel from four of the stents is extracted in dichloromethane solvent. The results of this extraction are presented in Table V below:

TABLE V

| | Paclitaxel content | | | |
| --- | --- | --- | --- | --- |
| Sample # | Paclitaxel conc. (mg/ml) | Paclitaxel content (µg) | Coating Wt. (µg) | µg Paclitaxel per µg coating |
| 1 | 30 | 111.7 | 676 | 0.17 |
| 2 | 30 | 50 | 627 | 0.08 |
| 3 | 30 | 45.3 | 612 | 0.07 |
| 4 | 30 | 37.4 | 602 | 0.06 |

Figure 8:
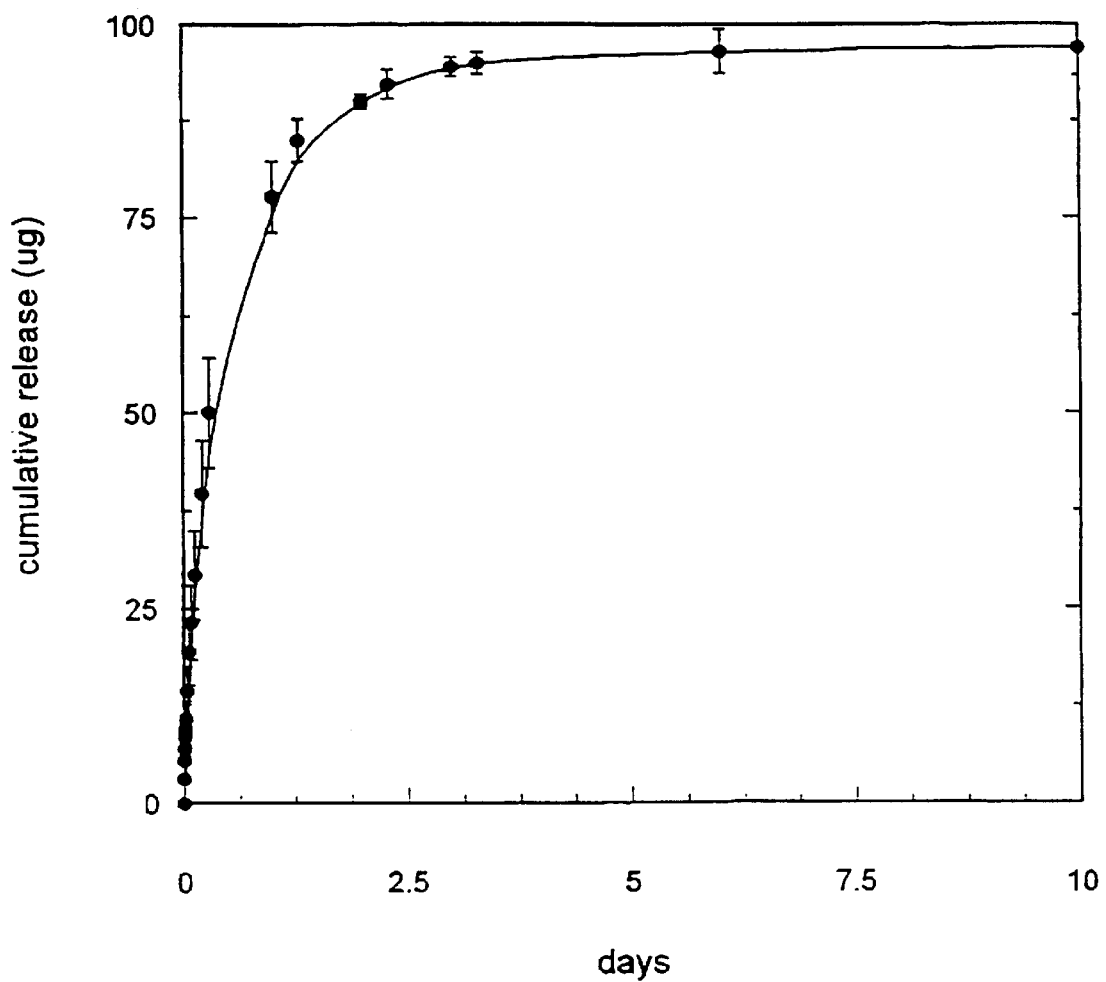
FIG. 8 shows the release profile of paclitaxel for up to 10 days from polyurethane coated stents dipped in 30 mg/ml paclitaxel in ethanol for 3 days, in accordance with the present invention.

The remaining three stents are immersed in a solution of phosphate buffered saline solution having pH 7.4 at 37° C. Cumulative release as a function of time is presented in FIG. 8.

EXAMPLE 9

Release Kinetics of Paclitaxel from Polyurethane-based Balloon Catheter Coating

Nylon balloons are coated with polyurethane by dipping into a 9 wt % solution of CHRONOFLEX® polyurethane in dimethylacetamide. The balloons are dried in a vacuum oven overnight at 50° C.

Each polyurethane coated balloon is loaded with paclitaxel either by dipping the coated balloon into a paclitaxel and ethanol solution or by dripping a known volume of a paclitaxel and ethanol solution onto the balloon surface.

In the first instance, a stock saturated solution of paclitaxel in ethanol is prepared. Then the polyurethane-coated balloon is inflated and submerged in the paclitaxel stock solution in a tube. The tube and balloon are well-sealed to prevent solvent evaporation. After remaining in the tube overnight, the ethanol is evaporated from the balloon over a suitable time period, such as about fifteen minutes. Five "dip-coated" balloons are prepared in this fashion.

In the second instance, a stock solution of paclitaxel having a concentration of 10 mg/ml prepared. Twenty ml of this paclitaxel stock solution are then pipetted onto an inflated polyurethane-coated balloon, providing a total mass of 200 mg of paclitaxel per balloon. Afterwards, ethanol is evaporated from the balloon over a suitable time period, such as about fifteen minutes. Five "drip-coated" balloons are prepared in this fashion.

Two drip-loaded balloons and two dip-loaded balloons are taken and the paclitaxel extracted in dichloromethane to determine total paclitaxel content. The paclitaxel content of the dip-coated balloons is found to be 1093+/−439 µg, while the drip-coated balloons are found to have 215+/−11 µg paclitaxel.

For comparison, nylon balloons are coated with paclitaxel/polyurethane by dipping the balloons into a dispersion of 14.5 wt % BAHYDROL® polyurethane (made by Bayer) and 2.6 wt % paclitaxel in a mixture of 73.6 vol % N-methylpyrrolidinone and 26.4 vol % water. Balloons are dried in a vacuum oven overnight at 50° C. The dried coatings contain 15% paclitaxel by weight. Nine balloons are formed. Seven balloons are tested for paclitaxel loading yielding an average of 196+/−44 µg paclitaxel after extraction in dichloromethane.

Figure 9:
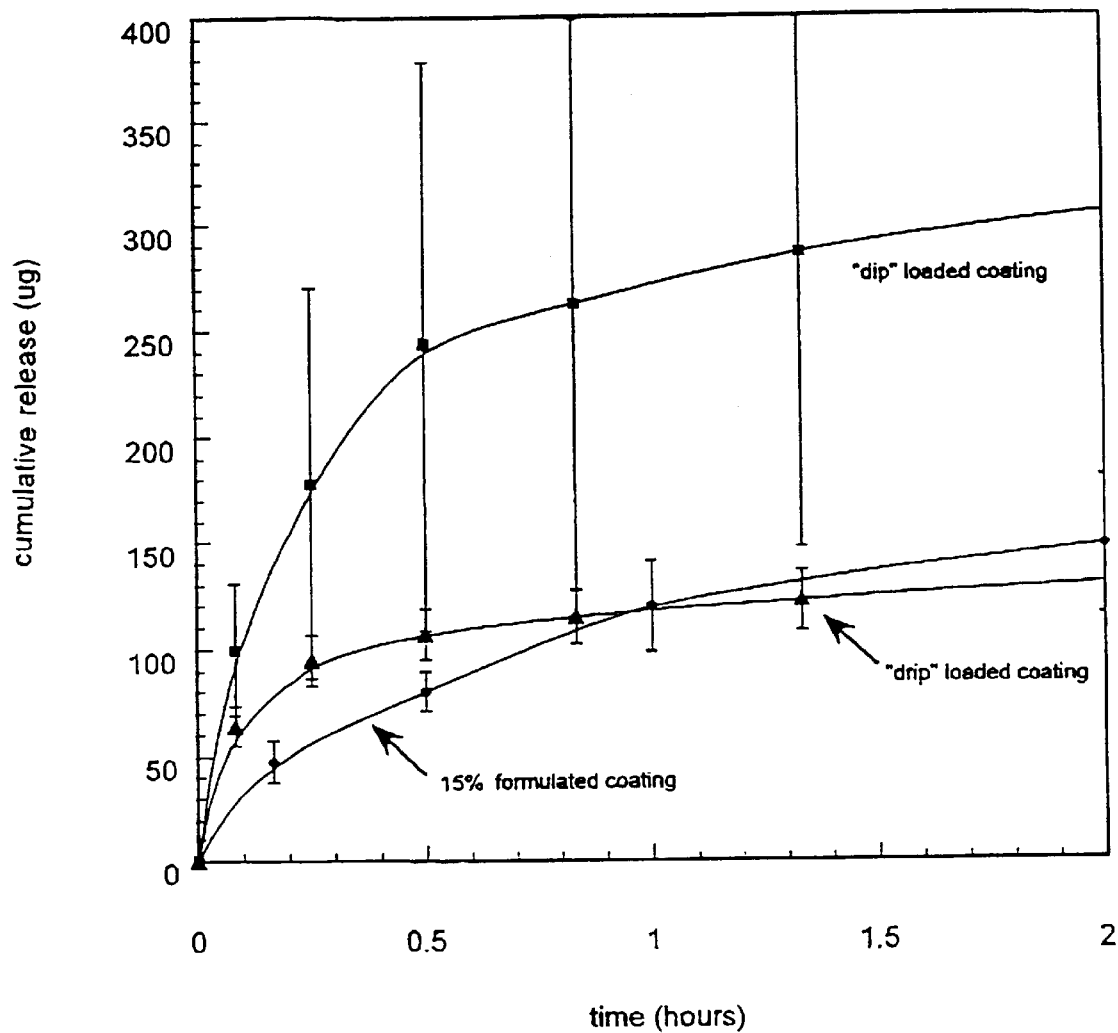
FIG. 9 shows the release profiles of paclitaxel from various polyurethane-coated balloon catheters for up to 2 hours, in accordance with the present invention.

The remaining three drip-loaded balloons from above, the remaining three dip-loaded balloons from above, and the remaining two balloons with the 15% paclitaxel formulated coating are placed in a solution of phosphate buffered saline solution having pH 7.4 at 37° C., and cumulative paclitaxel release is measured as a function of time. The results of this study are presented in FIG. 9.

EXAMPLE 10

Preparation of a Stent Coated with a Polylactic Acid/polycaprolactone(PLA/PCL) Copolymer/paclitaxel Matrix PLA/PCL copolymer obtained from Birmingham Polymers, Inc., Birmingham, Ala., was dissolved in chloroform. Paclitaxel obtained from Hauser, Inc. was then dissolved in the chloroform to form a solution having a 70/30 weight ratio of copolymer/paclitaxel. The solution was then sprayed onto the surface of a 9 mm long balloon-expandable stainless steel NIR® stent obtained from Medinol, Inc., Tel Aviv, Israel. Substantially all exposed surfaces of the stent were covered with the solution. The stent was then dried in a vacuum oven at 50° C. for approximately 2 hr. and a matrix of PLA/PCL copolymer having 200 μg of paclitaxel incorporated therein was thus formed as a coating on the stent. The paclitaxel component of the matrix comprised approximately 30% by weight of the matrix.

EXAMPLE 11

In-vitro Delivery of Paclitaxel to Porcine Coronary Arteries

A stent prepared as set forth in Example 10 was inserted via a balloon catheter and expanded into contact with a porcine coronary artery. In vitro, the stent delivered 2–3 μg/day of paclitaxel over a period of 28 days. In comparison to the same stent having no coating, after 28 days, a 50% reduction in the occurrence of neointimal hyperplasia was observed.

EXAMPLE 12

In-vitro Delivery of Paclitaxel to Rabbit Iliac

A stent prepared as set forth in Example 10 was inserted via a balloon catheter and expanded into contact with a rabbit iliac. In vitro, the stent delivered 2–3 μg/day of paclitaxel over a period of 28 days. In comparison to the same stent having no coating, after 28 days, a 70% reduction in the occurrence of neointimal hyperplasia was observed.

EXAMPLE 13

In-vitro Delivery of Paclitaxel to Rabbit Iliac

A stent prepared as set forth in Example 10 was inserted via a balloon catheter and expanded into contact with a rabbit iliac. In vitro, the stent delivered 2–3 μg/day of paclitaxel over a period of 56 days. In comparison to the same stent having no coating, after 56 days, a 60% reduction in the occurrence of neointimal hyperplasia was observed.

COMPARATIVE EXAMPLE 14

Coil Stents with Biocompatible Polymeric Material/TAXOL® Coating

The results presented in Table VI below were obtained by Leon et al., "TAXOL®-Coated Coronary Stents Potential to Reduce Proliferation," European Society of Cardiology, Vienna, Austria 1998. GR-II® coil stents, available from Cook Inc., Bloomington, Ind., were coated with a biocompatible polymeric coating incorporating 175–200 μg of TAXOL® and exhibiting in vitro release kinetics of 0.75 μg/day for the first 30 days. The stents were placed in porcine coronary arteries and the effect on neointima formation compared to that seen with control stents was analyzed. The results are shown in Table VI below:

TABLE VI

TAXOL ®-Coated Stents versus Control

|  | Control (N = 10) | TAXOL ®-coated Stent (N = 9) |
| --- | --- | --- |
| Reference Vessel Diameter (mm) | 2.9 ± 0.3 | 3.0 ± 0.2 |
| Stent/Artery | 1.1 ± 0.1 | 1.1 ± 0.1 |
| Diameter Stenosis (%) | 51 ± 27 | 27 ± 27* |
| Neointima Area (μm) | 669 ± 357 | 403 ± 197* |

*$p<0.05$ versus control

In contrast to the results obtained in Example 11 above using the NIR® non-coiled stent in a porcine coronary artery (neointimal hyperplasia reduction of 50%), the results obtained with a coil stent and paclitaxel (placed in a porcine coronary artery) show a neointimal hyperplasia reduction of only 40% calculated as follows: [(669–403)/669]×100= 40%.

COMPARATIVE EXAMPLE 15

Comparison of Low-dose and High Dose TAXOL®-coated Stents versus Control

The results of another study by Leon et al., "TAXOL®-Coated Coronary Stents: Potential to Reduce Proliferation," European Society of Cardiology, Vienna, Austria 1998 on the effect of coated coil stents on neointima formation using 2 doses of "fast-release" TAXOL® are shown in Table VII below: The results for both "low-dose" and "high-dose" TAXOL®-coated stents are shown in Table VII below:

TABLE VII

Low-Dose and High Dose TAXOL ®-Coated Stents versus Control

|  | Control (N = 12) | Low-Dose TAXOL ® (N = 10) | High-Dose TAXOL ® (N = 11) |
| --- | --- | --- | --- |
| Reference Vessel Diameter (mm) | 2.8 ± 0.2 | 2.8 ± 0.7 | 3.0 ± 0.3 |
| Stent/Artery | 1.16 ± 0.09 | 1.15 ± 0.07 | 1.14 ± 0.05 |
| Diameter Stenosis (%) | 34.8 ± 15.6 | 19.3 ± 9.45* | 15.1 ± 6.61*† |
| Neointima Area (μm) | 1.52 ± 0.78 | 1.07 ± 0.53 | 0.93 ± 0.5*† |

*$p<0.05$ versus control
†p = not significant versus low-dose TAXOL ®

In contrast to the results obtained in Examples 11–13 above using the NIR® non-coiled stent (neointimal hyperplasia reduction of from 50–70%), the above results obtained with a coated coil stent show a neointimal hyperplasia reduction of only 30% and 39%, respectively, calculated as follows: [(1.52–1.07)/1.52]×100=30% (low-dose TAXOL®) and [(1.52–0.93)/1.52]×100=39% (high-dose TAXOL®).

EXAMPLE 16

Preparation of a Vena Cava Filter Coated with a Polylactic Acid/polycaprolactone(PLA/PCL) Copolymer/paclitaxel Matrix A filter for placement in the vena cava for capturing blood clots is coated with a PLA/PCL copolymer/paclitaxel matrix in the manner substantially as set forth in Example 10. The filter is sized and constructed to be compressed and passed through the vasculature of a patient to be anchored against an inner wall surface of a blood vessel for capturing blood clots in a blood stream passing therethrough. The filter is described in International Application No. WO 96/17634.

EXAMPLE 17

Preparation of a Vena Cava Filter Coated with a Polylactic Acid/polycaprolactone (PLA/PCL) Copolymer/paclitaxel Matrix A filter for placement in the vena cava for capturing blood clots is coated with a PLA/PCL copolymer/paclitaxel matrix in the manner substantially as set forth in Example 10. The filter is also adapted for placement in a blood vessel for capturing blood clots in a blood stream passing therethrough. This filter is provided with struts that minimize the risk of vessel damage if the vessel is compressed asymmetrically. The filter is described in International Application No. WO 96/12448.

EXAMPLE 18

Preparation of a Vascular Graft Coated with a Polylactic Acid/polycaprolactone (PLA/PCL) Copolymer/paclitaxel Matrix A woven synthetic vascular graft for replacement of a segment a blood vessel is coated with a PLA/PCL copolymer/paclitaxel matrix in a manner substantially as set forth in Example 10. The vascular graft is ravel-resistant due to inclusion of a fusible component and self-supporting due to inclusion of a stiffening component. The vascular graft is described in U.S. Pat. No. 5,509,931.

It is to be appreciated that the parameters described in the above examples are merely illustrative and that the present invention is not so limited. For example, in each of the examples provided, any suitable polymer may be used for the polymer coating, any suitable drying time periods and temperatures may be used, any suitable organic solvent may be used, any suitable method for applying the polymer coatings to the medical devices may be used, any suitable method for applying the drugs to the polymer coatings may be used, any suitable water-insoluble analogue of the disclosed drugs may be used, and any suitable drug loading concentrations may be used.

The present invention provides a previously unknown method and medical device for the localized delivery of substantially water-insoluble drugs. The present invention provides, in one embodiment, a paclitaxel/polymer coated stent which has an extended release rate of from about 0.2 to about 7 $\mu$g per day, preferably in the range of from about 0.5 to about 5 $\mu$g per day over an extended period of at least about 28 days. In a preferred embodiment of the invention, there is provided a polymer/paclitaxel coated non-coiled stent which has an extended release rate of paclitaxel and which reduces neointima formation in injured blood vessels and other body lumens into which it is placed. The extended release rate is effective to prevent, decrease, eliminate, or modify cellular proliferation associated with neointima formation and/or other proliferative disease or disorder.

Those with skill in the art may recognize various modifications to the embodiments of the invention described and illustrated herein. Such modifications are meant to be covered by the spirit and scope of the appended claims.

We claim:

1. A method for preparing a patterned stent having paclitaxel coated thereon comprising the steps of:
   providing a polyvinyl aromatic polymer;
   providing a patterned stent;
   coating at least a portion of the exterior surface of the patterned stent with the polyvinyl aromatic polymer to form a polymer coating; and
   applying a drug solution to the polymer, said drug solution comprising paclitaxel dissolved in an organic solvent.

2. The method of claim 1, wherein said organic solvent is selected from the group consisting of ethanol, isopropanol, chloroform, acetone, pentane, hexane, methylene chloride, and mixtures thereof.

3. The method of claim 2, wherein said organic solvent further comprises water.

4. The method of claim 1, wherein said step of applying a drug solution to said polymer includes the step of dipping said polymer into said drug solution.

5. The method of claim 1, wherein said drug solution is applied to said polymer before said polymer is coated onto said patterned stent.

6. The method of claim 1, wherein said drug solution is applied to said polymer after said polymer is coated onto said patterned stent.

7. The method of claim 1, further comprising positioning said patterned stent at a desired location in a body lumen.

8. The method of claim 1, wherein said step of coating comprises applying multiple layers of said polymer to said patterned stent.

9. The method of claim 1, wherein said polyvinyl aromatic polymer is a copolymer.

10. A patterned stent for delivering a substantially water-insoluble drug at a desired location within a body, comprising
    a polyvinyl aromatic polymer coating containing paclitaxel provided on at least a portion of said patterned stent.

11. The patterned stent of claim 10, wherein said polymer coating is layered.

12. The patterned stent of claim 10, wherein the at least one water-insoluble drug comprises a combination of paclitaxel and an agent selected from the group consisting of anticoagulants, antimitotics, antithrombogenics, thrombolytics, anti-inflammatory agents, antioxidants, growth factors, modulators of vascular homeostasis, cytocidal agents, and cytostatic agents.

13. The patterned stent of claim 10, wherein the paclitaxel is released from said stent over a time frame effective to inhibit proliferative disease when said stent is positioned at a site of injury to thereby prevent or inhibit undesired cellular proliferation.

14. The patterned stent of claim 13, wherein the time frame is at least about 7 days.

15. The patterned stent of claim 13, wherein the time frame is at least about 28 days.

16. The patterned stent of claim 13, wherein the paclitaxel is released at a rate in the range of from about 0.2 to about 7 $\mu$g paclitaxel per day.

17. The patterned stent of claim 13, wherein the paclitaxel is released at a rate in the range of from about 0.5 to about 5 µg per day.

18. The patterned stent of claim 10, wherein the stent inhibits neointimal proliferation when placed at the site of injury in a blood vessel.

19. The patterned stent of claim 10, wherein said polyvinyl aromatic polymer is a copolymer.

20. A method of preventing or inhibiting proliferative disease at a site of blood vessel injury in a patient comprising implanting a patterned stent comprising an outer coating of polyvinyl aromatic polymer/paclitaxel at the site of injury, wherein the paclitaxel is released from the outer coating at a release rate sufficient to inhibit or prevent cellular proliferation at the site of injury.

21. The method of claim 20, wherein the paclitaxel is released from the outer coating at a release rate of from about 0.2 to about 7 µg/day.

22. The method of claim 20, wherein the paclitaxel is released from the outer coating at a release rate and for a period of time sufficient to inhibit or prevent neointima formation at the site of injury.

23. The method of claim 20, wherein the proliferative disease is restenosis.

24. The method of claim 20, wherein the proliferative disease is restenosis.

25. The method of claim 20, wherein said polyvinyl aromatic polymer is a copolymer.

26. A method of preventing or inhibiting proliferative disease in a patient comprising implanting a patterned stent comprising an outer coating of polyvinyl aromatic polymer/paclitaxel at the site of cellular proliferation, wherein the paclitaxel is released from the outer coating at a release rate and for a period of time sufficient to inhibit or prevent cellular proliferation at the site.

27. The method of claim 26, wherein the paclitaxel is released from the outer coating for a period of time from about 7 to about 28 days.

28. The method of claim 26, wherein the paclitaxel is released from the outer coating at a release rate of from about 0.2 to about 7 µg/day.

29. The method of claim 26, wherein the paclitaxel is released from the outer coating at a release rate and for a period of time sufficient to inhibit or prevent neointima formation at the site.

30. The method of claim 26, wherein the proliferative disease is restenosis.

31. The method of claim 26, wherein said polyvinyl aromatic polymer is a copolymer.

32. A catheter for delivering substantially water-insoluble drugs to a desired location within a body lumen, said catheter comprising:

a shaft;

an expandable portion mounted on said shaft, said expandable portion including an inflatable balloon and a sheath member extendable over said expandable portion;

a polyvinyl aromatic polymer coating on at least a portion of said expandable portion of said catheter, said polymer coating being impregnated with paclitaxel.

33. The catheter of claim 32 wherein said polymer coating is leyered.

34. The catheter of claim 32 further comprising an agent selected from the group consisting of anticoagulants, antimitotics, antithrombogenics, thrombolytics, anti-inflammatory agents, antioxidants, growth factors, modulators of vascular homeostasis, cytocidal agents and cytostatic agents.

35. The catheter of claim 32 wherein the paclitaxel is released from said catheter over a time frame effective to inhibit proliferative disease when said catheter is positioned at a site of injury to thereby prevent or inhibit undesired cellular proliferation.

36. The catheter of claim 35 wherein the time frame is at least about 7 days.

37. The catheter of claim 35 wherein the time frame is at least about 28 days.

38. The catheter of claim 35 wherein the paclitaxel is released at a rate in the range of from about 0.2 to about 7 µg paclitaxel per day.

39. The catheter of claim 35 wherein the paclitaxel is released at a rate in the range of from about 0.5 to about 5 µg per day.

40. The catheter of claim 35, wherein the catheter inhibits neointimal proliferation when placed at the site of injury in a blood vessel.

41. The catheter of claim 32, wherein said polyvinyl aromatic polymer is a copolymer.

42. A patterned stent for delivering a substantially water-insoluble drug at a desired location within a body, comprising a polyvinyl aromatic polymer coating containing at least one substantially water-insoluble drug provided on at least a portion of said patterned stent, wherein said substantially water-insoluble drug comprises a combination of paclitaxel and an agent selected from the group consisting of anticoagulants, antimitotics, antithrombogenics, thrombolytics, anti-inflammatory agents, antioxidants, growth factors, modulators of vascular homeostasis, cytocidal agents, and cytostatic agents.

43. The patterned stent of claim 42, wherein said polyvinyl aromatic polymer is a copolymer.

* * * * *